United States Patent [19]
Welling et al.

[11] Patent Number: 6,107,033
[45] Date of Patent: Aug. 22, 2000

[54] METHODS AND MATERIALS FOR DETERMINING RELATIVE ABUNDANCE OF MICROORGANISMS IN MIXED POPULATIONS

[75] Inventors: Gjalt Wietze Welling, Roderwolde; Frederik Schut, Groningen; Petra Simone Langendijk, Nijmegen; Gijsbert Johan Jansen, Groningen; Michael Hendrik Francis Wilkingson, Groningen; Peter Elffrich, Groningen, all of Netherlands

[73] Assignees: Rijksuniversiteit Groningen; Microscreen B.V., both of Netherlands

[21] Appl. No.: 09/000,291

[22] PCT Filed: Jul. 29, 1996

[86] PCT No.: PCT/NL96/00306

§ 371 Date: Aug. 13, 1998

§ 102(e) Date: Aug. 13, 1998

[87] PCT Pub. No.: WO97/05282

PCT Pub. Date: Feb. 13, 1997

[30] Foreign Application Priority Data

Jul. 28, 1995 [EP] European Pat. Off. ............. 95202070

[51] Int. Cl.$^7$ ...................................... C12Q 1/68
[52] U.S. Cl. .................... 435/6; 435/5; 435/8.1; 436/501; 536/23.1; 536/24.1; 536/24.3; 536/24.31; 536/24.32; 536/24.33; 935/77; 935/78
[58] Field of Search ................. 435/6, 5, 8.1; 436/501; 536/23.1, 24.1, 24.3, 24.31, 24.32, 24.33; 935/77, 78

[56] References Cited

U.S. PATENT DOCUMENTS 5,679,520 10/1997 Hogan et al. ............................... 435/6

FOREIGN PATENT DOCUMENTS 0497464 1/1992 European Pat. Off. .................. 435/6

OTHER PUBLICATIONS

Giovannoni et al. Phylogenetic Group–Specific Oligodeoxynucleotide Probes . . . Journal of Bacteriology. Feb. 1988, vol. 170, No. 2. p. 720–726.

*Primary Examiner*—Kenneth R. Horlick
*Assistant Examiner*—Janell E. Taylor
*Attorney, Agent, or Firm*—Michaelson & Wallace; Peter L. Michaelson; Edward M. Fink

[57] ABSTRACT

The present invention relates to a method for determining the relative abundance of individual species or lower phylogenetic subgroups of microorganisms in a mixed population of several microorganisms comprising the steps of: 1) providing a set of labeled in situ hybridization cluster oligonucleotide probes; 2) hybridization of said probes with a sample of the mixed population, and 3) quantitative analysis of the number of labeled microorganisms. Further it relates to a method for analyzing dynamics in relative abundance of individual microorganisms in a mixed population. Further it relates to a set of probes which are cluster specific and which are provided with at least one label for use in a method of the invention and to a kit of parts for determining the relative abundance of individual species of microorganisms in a mixed population of several microorganisms comprising such probes which together with suitable materials for pre-treating the sample and/or suitable materials for carrying out hybridization and/or suitable materials for analysis of the result of the hybridization.

16 Claims, 4 Drawing Sheets

Figures 1, 1A:
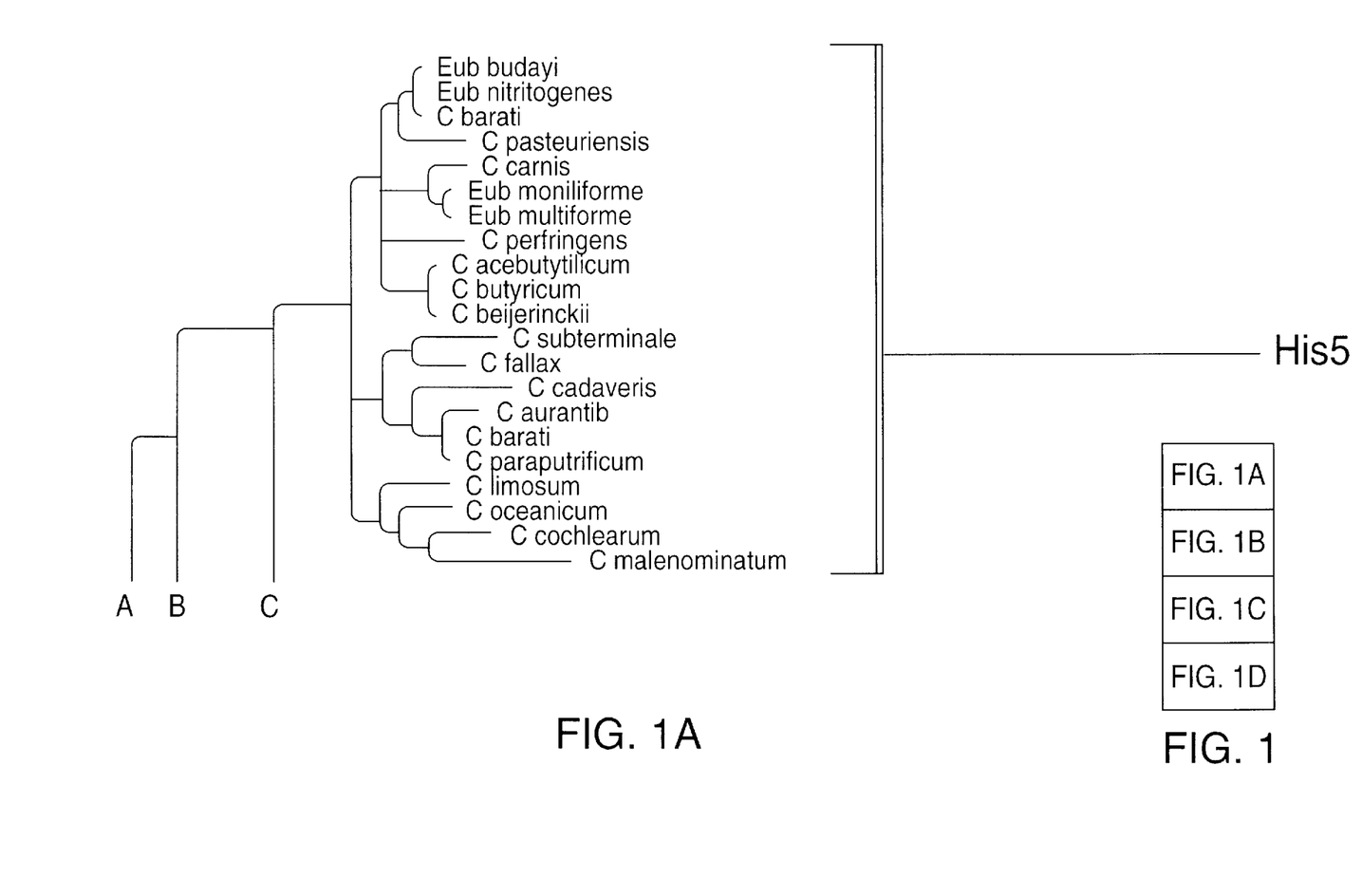
Figure 1B:
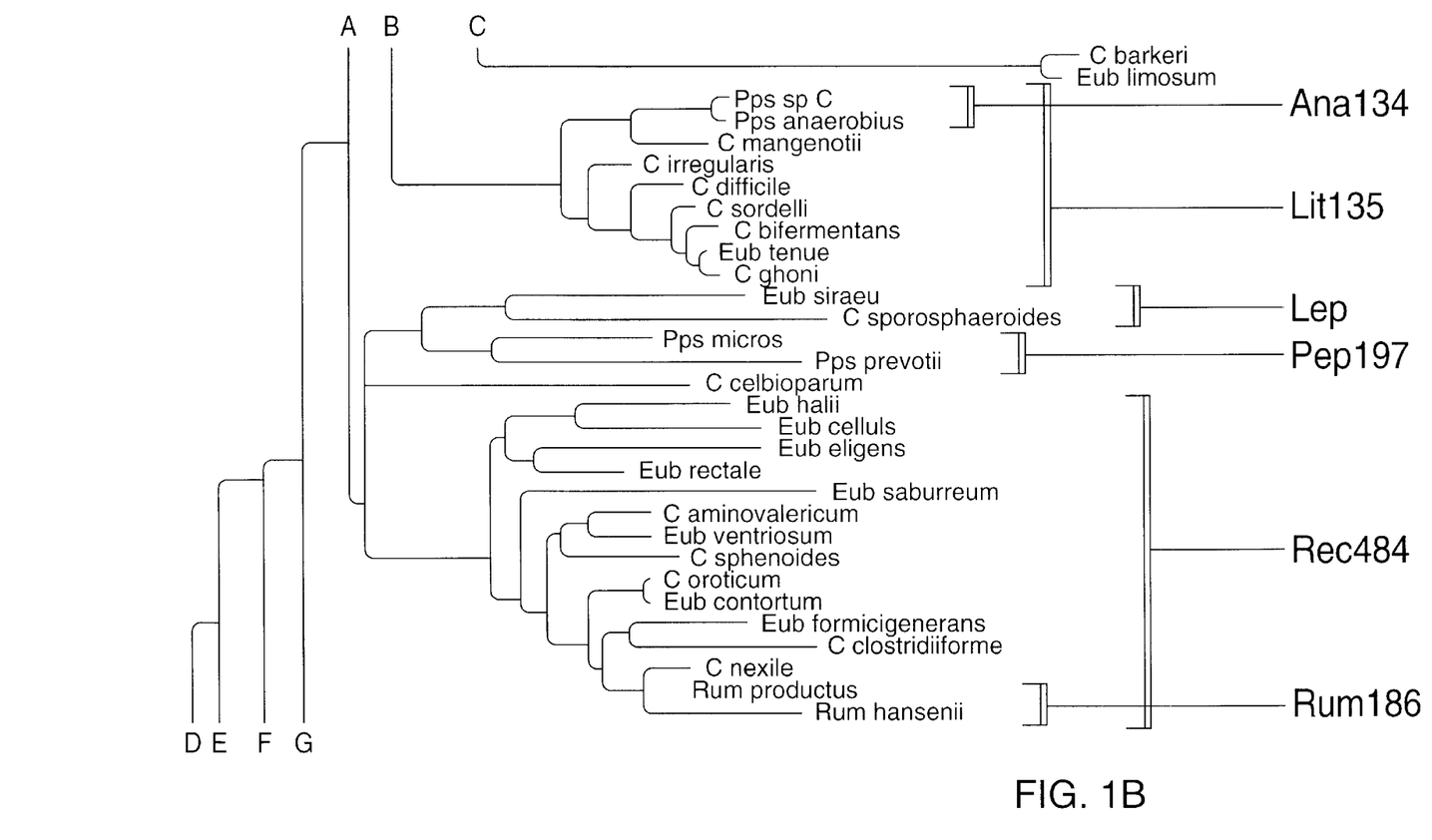
Figure 1C:
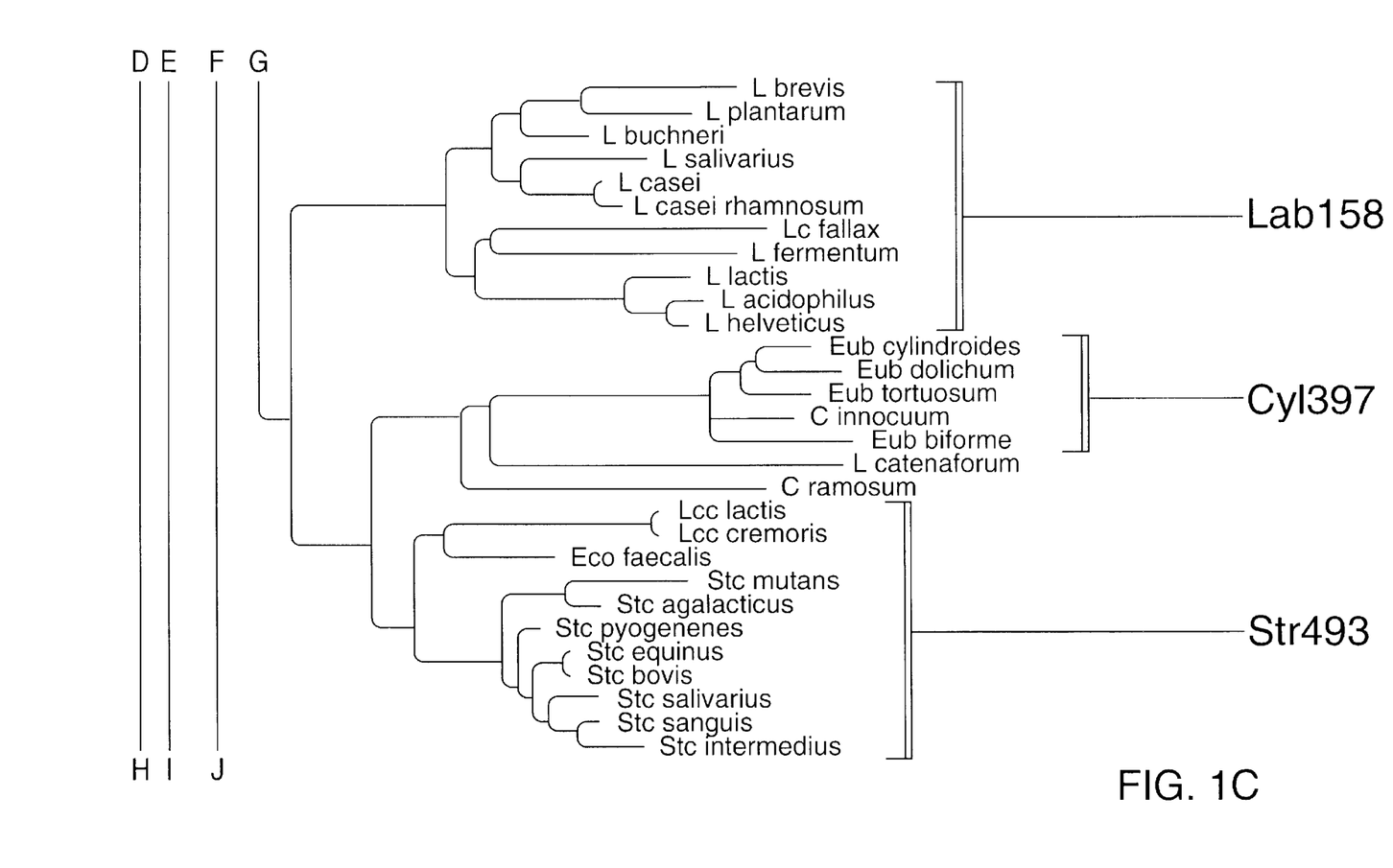
Figure 1D:
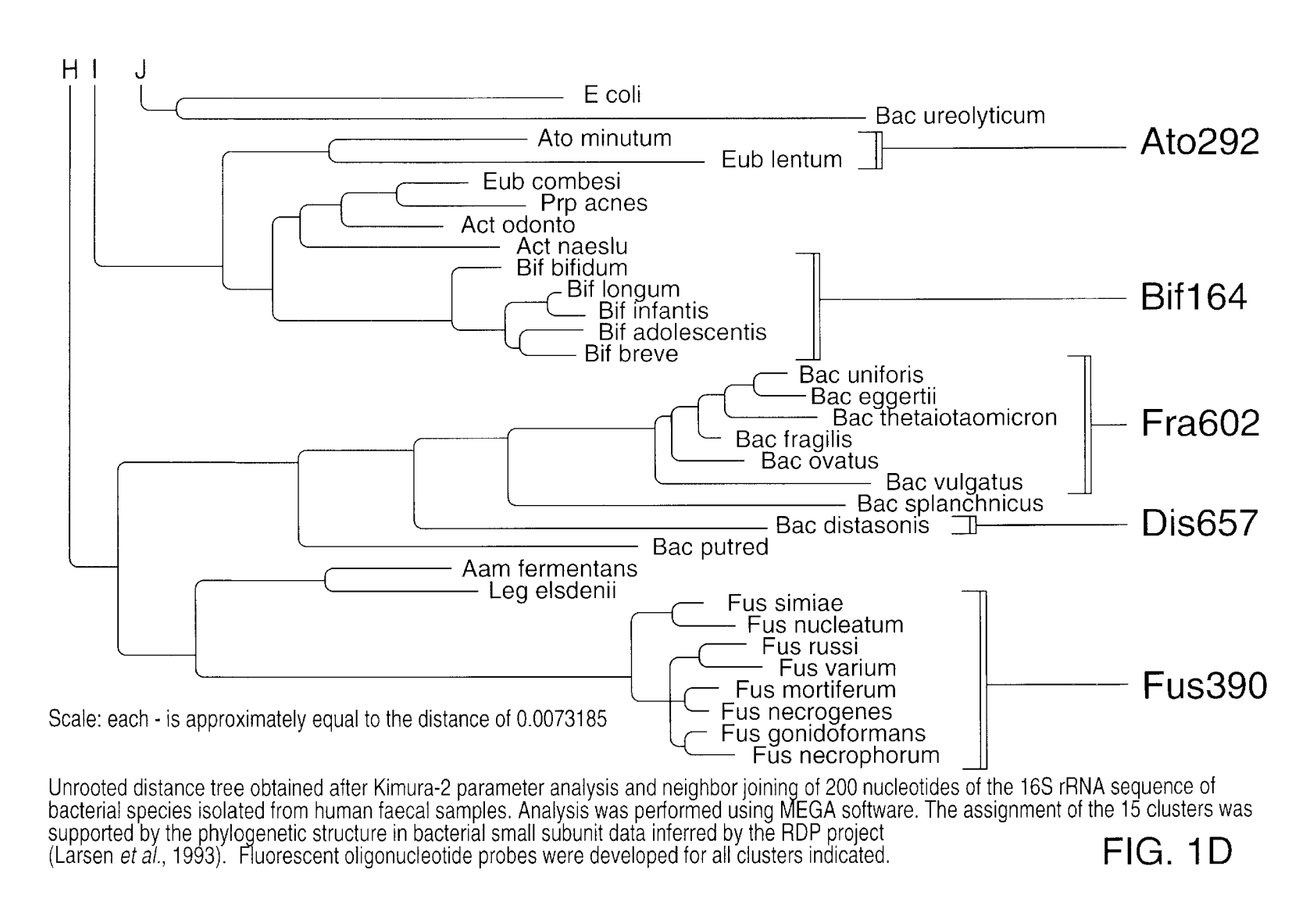

Unrooted distance tree obtained after Kimura-2 parameter analysis and neighbor joining of 200 nucleotides of the 16S rRNA sequence of bacterial species isolated from human faecal samples. Analysis was performed using MEGA software. The assignment of the 15 clusters was supported by the phylogenetic structure in bacterial small subunit data inferred by the RDP project (Larsen et al., 1993). Fluorescent oligonucleotide probes were developed for all clusters indicated.

Scale: each - is approximately equal to the distance of 0.0073185

METHODS AND MATERIALS FOR DETERMINING RELATIVE ABUNDANCE OF MICROORGANISMS IN MIXED POPULATIONS

The invention relates to methods and materials for determining the relative abundance of individual microorganisms in mixed populations of microorganisms, in particular to such methods for determining relative abundance of individual microorganism species in the indigenous gut flora, especially of humans.

Such methods have not been available until the present invention. What has been possible until the present invention is determination of the presence of individual microorganism species in a mixed population such as the intestinal flora.

Traditional methods to determine the composition of the intestinal flora require culturing of the microorganisms in the population on both selective and non-selective media. These methods are laborious and time consuming, which in itself makes it hardly possible to do anything beyond identifying the microorganisms present in the mixed population. Furthermore these methods are prone to methodological and statistical error. Another barrier for determination of abundance of one microorganism via à vis others (relative abundance) is that culturing includes multiplication of the microorganisms which of course do not divide at the same rate. Therefore determination of relative abundance is practically not possible using these methods, let alone that the dynamics of such a population through time could be followed.

The composition and activity of the indigenous gut flora is of paramount importance to human immunology, nutrition, pathogenesis and hence to health of individuals (Van der Waaij et al., 1971). Colonization resistance, or bacterial antagonism of the indigenous intestinal microflora for instance represents a first line of defence against the establishment of pathogenic microorganisms in the intestinal tract (Van der Waaij et al., 1971; 1989).

The human (mammalian) intestinal tract is not the only mixed population of microorganisms for which measuring the relative abundance of individual species or other subgroups of microorganisms is useful or important.

In industry, specifically in the food sector and fermentation industry, monitoring of the bacteria- or yeast-dependent fermentation process is essential for quality assurance both with respect to hygiene and product stability. Environmentally, monitoring of complex mixed bacterial populations is elemental in predicting the effectiveness of bioremediation in soil-, gas- and waste water-treatment. Environmental microbiologists are in need for tools that explain nutrient regeneration potentials in terms of biomass of individual metabolic clusters of bacteria.

Although much is known of the physiology of most bacterial species individually and of metabolic activities of mixed bacterial consortia as a whole, factors that determine their abundance and those causing subtle as well as dramatic changes in population composition have remained largely unknown due to the technical limitations of the classical cultivation and identification techniques. Therefore, rapid monitoring techniques that can unravel the population compositions of complex mixed bacterial consortia are of great scientific importance.

The invention thus provides a rapid and reliable method for determining the relative abundance of individual species or lower phylogenetic groups of microorganisms in a mixed population of several microorganisms comprising the steps of:

1) providing a set of labelled in situ hybridization cluster oligonucleotide probes;
2) hybridization of said probes with a sample of the mixed population, and
3) quantitative analysis of the number of labelled microorganisms.

In situ hybridization in itself is a well known technique, as can be read from EP-A-0 497 464, which relates to in situ hybridization techniques using fixed, permeabilized but not mounted cells. The method is used to determine the presence of single microorganisms. So far in situ hybridizaton has however not been applied to determine the relative abundance of lower phylogenetic subclasses, let alone following the dynamics of a mixed population of microorganisms. Labelled probes are an essential part in in situ hybridization. The present invention provides a set of cluster probes which have been chosen in an unexpected novel manner, i.e. not based on the normal taxonomic principles. A set of cluster probes for the purposes of this invention is defined as a set of oligonucleotides capable of identifying microorganisms from a cluster, such as a species, a genus or another lower phylogenetic subgroup. Preferably these probes are all based on a comparable target nucleic acid of the different microorganism in the mixed population, in this case for example the 16S rRNA.

Cluster-probes have received most attention in aquatic and soil microbiology. The limitations of using culture-dependent methods for studying the diversity and ecology of natural microbial communities are well known in these fields since most (>99%) of the bacteria present in these habitats are non-culturable and of unknown taxonomic identity. As a consequence, the use of more direct molecular characterizations has become more common in this field. A recent review (Amann et al., 1995) summarizes many of the lower group level/genus level proves developed thus far. Invariably, these probes find their application in the environmental fields of waste water and sediment microbiology. Upper group level probes (such as Proteobacterial subclass probes) and domain level probes (used to distinguish between archea, bacteria and eucarya) have limited descriptive value since they "cover" too many different evolutionary lines of descent. The application of species-level probes in the analysis of the community structure of complex mixed bacterial assemblages will probably make the method equally time consuming as traditional cultivation techniques.

These types of cluster probes are therefore not suitable for the present invention. In the field of regular use of cluster probes nobody has contemplated using lower phylogenetic cluster probes, let alone that anyone would have applied such probes to the field of determining the relative abundance of microorganisms in human intestinal flora.

These 16S rRNA probes are a preferred embodiment of the present invention.

With increasing frequency, 16S-rRNA targeted hybridisation probes in combination with PCR-amplification of target DNA, are applied for the detection of specific bacterial taxa in mixed bacterial populations. Currently, by using PCR techniques the qualitative presence of a single cell against a background of $10^9$ non-target cells can be confirmed. As such the technique is extremely sensitive. However, the technique gives little or no quantitative information on absolute cell numbers. Fluorescence in situ hybridisation with a set of phylogenetic cluster probes is superior to PCR with respect to enumeration of individual cells that belong to a certain bacterial group. This technique is also superior to the DGGE-technique for mixed population analysis of which PCR forms an integrated part.

Approximately 100 bacterial species out of ±400 dominate the culturable (and thus identified) population. The 16S rRNA sequences of most of these bacterial are currently know. There is more than sufficient sequence data to design specific probes for predominant groups of faecal bacteria. We report the development of a set of 15 16S rRNA targeted oligonucleotide probes with which the predominant bacterial groups of the human intestinal micro flora can be enumerated in situ.

The probes are preferably labelled with fluorescent materials. This allows for microscopic analysis combined with preferably automated image analysis.

For the detection of fluorescent oligonucleotide probes hybridized to bacteria on microscopic slides, photography can be applied. However, quantification by this method is hampered by the absence of an objective threshold criteria for the discriminating between hybridized and nonhybridized cells. Therefore, for objective evaluation of probe specificity, an image analysis system is employed which allows fluorometrical measurement of individual cells. All details of the hardware and software of this system have been published elsewhere (see refs. 32–34 in Bifidobacterium-paper of Langendijk et al., August 1995).

Also preferred is an embodiment where probes identifying a certain species are provided with a different label than other probes identifying other species. This reduces the number of assays and/or samples to be taken.

The invention also provides probes and kits for carrying out the methods according to the invention.

The kits will usually comprise probes and other reagents for in situ hybridization, as well as other reagents for pretreating samples and/or post treating samples.

APPLICATION OF THE INVENTION

In such a kit, the probes may be labelled with fluorescein-5-isothiocyanate (FITC) at the 5'-end. Other labels may be attached to either 3'- or 5'-end of these probes, to both ends or internally.

Among these labels can be
1) Direct fluorescent labels:
FLUOS (5(6)-carboxyfluorescein-N-hydroxysuccimide-ester)
TRITC (tetramethylrhodamine-5-isothiocyanate)
AMCA (7-amino-4-methylcoumarin-3-acetic acid)
Texas red
Indocarbocyanine dyes such as CY3, CY5 or $CY_7$
Any other fluorescent label.
2) Indirect labels:
Enzymes such as alkaline phosphatase (AP) or horseradish peroxidase (HRP) either attached directly or via a C6 thiol linker and used in combination with chemiluminescent substrates like AMPPD (3-('-spiroadmantane)-4-methoxy-4-(3'-phosphoryloxy)-phenyl-1,2-dioxethane) or fluorescence-generating substrates.
Digoxigenin
in combination with anti-DIG antibodies labelled with gold particles
fluorescent labels such as carboxyfluorescein or carboxyrhodamine 101
enzymes such as alkaline phosphatase (AP) or horseradish peroxidase (HRP) in combination with chemiluminescent substrates like 3-(2'-spiroadamantane)-4-methoxy-4-(3'-phosphoryloxy)-phenyl-1,2-dioxethane (AMPPD) or fluorescence-generating substrates.
Biotin
in combination with avidin or streptavidin and labelled as the anti-DIG antibodies
Dinitrophenyl (DNP) as hapten
in combinaiton with appropriate antibodies and labelled as the anti-DIG antibodies
or any indirect label.

Further objects of the invention are:
To study the effect of novel foods (prebiotics), probiotics and functional foods on the intestinal microflora of both man and animal;
To study the effect of antibiotics on the intestinal microflora of both man and animal;
To monitor the development of mixed microbial populations that are involved in industrial fermentation processes (cheese and other (dairy) fermentation products, beer, wine etc);
To rapidly detect microbial contamination in product or production tools from raw material to end product (hygiene control);
To identify and quantify the presence and activity of micro-organisms in waste water treatment systems;
To identify and quantify the presence and activity of micro-organisms in bioremediation processes;
To identify and quantify the presence and activity of micro-organisms in marine systems;
To determine the microbial status of (polluted) soils, waters, gases etc;
To determine the status of potable water, swimming water and surface water with respect to pathogenic bacteria and human health;
To study the effect of registered and novel medicines on the intestinal microflora of both man and animal;
To perform diagnostics/rapid detection of pathogenic infections in man and animal including livestock;
To detect bacterial resistance to antibiotics;
To study the effect of homeopathic preparations and reform products on the intestinal microflora of both man and animal;
To detect specific tooth-decay generating oral *streptococci* for the toothpaste industry;
To detect pathogens or consortia of microorganisms that are either detrimental or beneficial to (crop) development, yield or quality during production, harvest, storage and transport.

The invention is further illustrated in the following detailed description.

DETAILED DESCRIPTION OF THE INVENTION

Development of the set of gut flora cluster-probes

In order to elucidate the population composition of complex mixed bacterial populations, aerobic and anaerobic cultivation techniques on solidified media are routinely employed. Standard identification protocols or commercially available test systems are subsequently used to identify the isolated strains. Although it is relatively easy to obtain a total viable count, counting of individually identifiable bacterial species is laborious and time consuming. Viable counts of the various aerobic and facultatively anearobic species can be obtained by using selective media. However, such media are not available for most strictly anaerobic species of the gut flora. Since some 30–40 species account for 99% of the human gut flora, several hundreds of isolates from each individual sample have to be identified in order to provide reliable population statistics. Furthermore, fermentation end-product analysis in isolated pure cultures is often essential for reliable identification. As a result, studies on population dynamics of the intestinal flora are often limited in the number of subjects or the number of species investigated and, as a consequence, the observed changes in composition are often not statistically significant. The recent increase in the production of designer foods (functional foods, pre- and probiotics) has lead to a demand for tools to study the effect of these products on the human intestinal microflora. We have developed such a tool by combining several innovative microbiological techniques such as fluorescence in situ hybridization and image cytometry.

Specifically, we have developed 16S rRNA targeted oligonucleotide probes for the enumeration of various phylogenetic groups of intestinal bacteria. These probes are used in fluorescence in situ hybridization studies on population dynamics. We have developed these probes after demonstrating the presence of fifteen major phylogenetic subpopulations within the intestinal microflora (FIG. 1).

Image Analysis and FISH

Whole cell in situ hybridization with 16S rRNA targeted, fluorescently labelled, synthetic oligonucleotides facilitates rapid determination of the taxonomic position of individual, even unculturable cells and allows accurate description of bacterial populations on a quantitative basis via automated microscopic image analysis. With the combination of these two techniques, it is possible to measure the fluorescence of specific cell-types quantitatively. The use of image analysis enables quantification of even very low fluorescent signals and ensures objective (researcher—independent) evaluation hybridization results. Automated recognition and enumeration of hybridized cells is facilitated by the use of image analysis software developed in our department (Meijer et al., 1991; Wilkinson, 1994; Wilkinson et al., 1993, 1994).

During an extensive study, using cultural methods of enumeration, some 200 species of bacteria have been isolated from human faecal samples (Finegold et al., 1974). Approximately 30 of these are numerically important and represent 10 distinct genera. Genus specific probes could thus prove appropriate in describing community structures at large. However, the natural classification system for bacteria, based on phenetic characteristics, is known no to comply fully with generically based methods; not all taxonomic genera are monophyletic on the basis of their 16S rRNA sequence, Eubacterium spp., for example, are clustered with several Clostridium and Peptostreptoccus spp., and peptostreptococel themselves are spread over several distinct phylogenetic clusters (FIG. 1), within these phylogenetic clusters, however, conserved regions can be identified and 16S rRNA probes designed for such regions can be used to identify the majority of the population to a well defined taxonomic level. Only a limited number of probes is thus required for the enumeration of the various phylogenetic groups of the gut flora (FIG. 1).

Although many copies of the ribosome should ensure sufficient signal, reality is often far from ideal. The accessibility of the target region, the number and kind of fluorochromes attached to the probe, the hybridization temperature, the metabolic status of the cells and the level of autofluorescence of non-target cells are important factors in obtaining sufficient specific fluorescent signal. Optical aid in the form of CCD-camera's is often required for small and slowly growing cells with little rRNA. Image analysis can be very helpful in discriminating between non-fading autofluorescence and rapidly fading fluorochrome fluorescence. Using such fluorescence lifetime imaging techniques, only a few positively hybridized cells can be distinguished among several thousand non-target cells in a microscope field (manuscript in preparation). This is necessary to enumerate those bacterial clusters that form a minority of the population, (e.g. Streptococci).

MATERIALS AND METHODS

Maintenance of Cultures

Bacterial cultures were maintained in anoxic Chopped Meat Carbohydrate medium (CMD) (Holdeman et al., 1977) at room temperature with bi-monthly transfers, and in anoxic skimmed milk at −20° C. Prior to hybridization, fresh cultures were grown in anoxic Peptone/Yeast extract/Glucose medium (PYG) (Holdeman et al., 1977) at 37° C.

Development of Probes

The 16S rRNA sequence of 113 species of faecal bacteria was retrieved from the RDP database version of Jun. 18, 1994 (Larsen et al., 1993). Together, these species represented most bacteria known to occur in human faeces (Drasar and Barrow, 1985). A Kimura 2 parameter distance analysis of the aligned sequences of these bacteria was performed with the Molecular Evolutionary Genetics Analysis (MEGA) program of Kumar et al. (1993), version 1.02. The obtained distance tree (Neighbour Joining) of the various species in phylogenetic clusters was compared to the phylogenetic grouping of the RDP database (Larsen et al., 1993). No significant cluster differences were found. Fifteen clusters were thus identified (FIG. 1). Unique sequences for each of the separate clusters were identified and an estimate was obtained of the number of cells in an average faecal sample that would hybridize with a probe for that cluster. Probe specificity was considered useful if the positively hybridizing part of the population was between 1% and 25%. In the case that a single species was expected to consist a major part of the total gut flora population, a species-specific probe as developed for that species.

Testing of Probe Specificity

Specificity of the probes was tested against the complete RDP database using the Check Probe command (Larsen et al., 1993) and was considered sufficient if a minimum of two mismatches with bacteria from all of the phylogenetic clusters of faecal bacteria was confirmed. Furthermore, a reference collection of 86 bacteria (table 1), representing a subset of the 113 species included in the target identification procedure (FIG. 1), was cultured and whole cell in situ hybridizations with these 86 species were performed. To this end, exponentially growing cells were fixed with 3% (v/v) formaldehyde. After 10 min storage at 4° C., 10 $\mu$l of fixed cell-suspension was applied to a glass slide that was pre-treated with Vectabond™ (Vector Laboratories, Burlingame, Calif.) to ensure proper adhesion of the cells. After drying for 20 min. at 45° C., the dried cell smears were dehydrated in a graded ethanol series (50%, 75% and 98% ethanol, v/v; 2 min.). Twelve $\mu$l of 0.2 $\mu$m pore-size filtered hybridization buffer was added to the cell smears. The hybridization buffer consisted of 0.9 M NaCl, 20 mM Tris-HCl (pH 7.5) and 0.1% (w/v) sodium dodecyl sulphate. After addition of 8 ng, $\mu l^{-1}$ FITC-labelled probe, the smears were covered with a coverslip. The slides were incubated in a buffer-saturated hybridization chamber at 45° C. for 15–20 h. After hybridization, the slides were washed for 15 min. in 50 ml hybridization buffer at 45° C., air-dried and the cell smears were embedded in mounting fluid consisting of a 1:1 mixture of glycerol and PBS (8 g 'l$^{-1}$ NaCl, 0.2 g 'l$^{-1}$ KCL, 1.44 g 'l$^{-1}$ Na$_2$HPO$_4$, 0.24 g 'l$^{-1}$ KH$_2$PO$_4$), supplemented with 2.5% (w/v) NaI.

the slides were evaluated by using an Orthoplan™ epifluorescence microscope (Leitz, Germany) equipped with a Hg arc lamp (HBO 100W, Osram, Germany), a 50x PL fluotar objective )Leitz), an I2/3 (blue excitation) filter block and a cooled CCD video camera (Loral, Fairchild CCD 5000/L, Sunnyvale, Calif. ). An exposure extension system for this camera was described previously (Wilkinson et al., 1993). The iamge analysis software used was the Groningen Reduction of Image Data (GRID) system (Meijer et al., 1991; Wilkinson et al., 1994). The fluroescence measurements were performed using the immunofluorescence package described previously (Jansen et al., 1993). Surface fluorescence signals were calibrated by using a non-fading uranyl glass reference (16). A phase-contrast and fluorescence image of each field of view were obtained. The shape of each bacterium was determined from the phase-contrast image automatically. The fluorescence of each object was determined from the corresponding area in the fluorescence image. This procedure avoids exclusion of non-fluorescent objects. The fluorescent images were recorded with a camera exposure-time of 12 sec. Per microscopic slide, 250–500 objects were measured. For each slide, the negative control (autofluorescence) was determined and the 95th percentile of its fluorescence distribution served as a threshold. The percentage of positively-hybridized objects, with fluorescence above the threshold, per total number of objects detected under phase-contrast illumination was dubbed the hybridization percentage. This percentage was determined to evaluate the performance of the probes and was done on pure cultures.

Whole cell in situ hybridisation and enumeration of phylogenetic clusters in faecal samples For quantification of phylogenetic clusters and total anaerobes in faeces, stool specimens from healthy human volunteers were collected and processed as follows. One gram of freshly defecated and homogenized faeces was suspended in 9 ml of 0.2 μm pore-size filtered PBS. This suspension was diluted 10× in filtered PBS and thoroughly mixed. After removal of debris (350×g; –min) the supernatant was collected and fixed overnight at 4° C. with 4% (w/v) fresh paraformaldehyde solution. Cells from 1 ml of fixed cell-suspension were washed twice (8,000 ×g; 5 min) in 1 ml of filtered PBS and resuspended in 1 ml of a mixture of PBS and ethanol (1:1). After 1 h of storage at –20° C., 5 μl of cell suspension was added to 50 μl pre-warmed (50° C.) hybridization buffer and 5 μl of FITC-labelled probe was added. Cells were hybridized for 16 h at 50° C. After resuspension in 10 mil hybridization buffer, cells were filtered on a 0.2 μm pore-size Isopore™ polycarbonate membrane filter (Millipore Corporation, U.S.A.) and washed twice with 10 ml of warm (50° C.) hybridization buffer. Filters were mounted on microscope slides with Vectashield™ and hybridized cells were counted visually using an Olympus BH2 microscope with a DPlanApo100UVPL objective (100x, N.A. 1.30), an HBO100 high pressure mercury vapour lamp, and an IB blue light excitation block with an extra EY455 excitation filter. The total number of bacteria present in faeces was determined by the method of Porter and Feig (1980), using 0.5 μg. ml$^{-1}$ (w/v) 4',6-diamidino-2-phenylindole (DAPI) as a DNA stain under illumination with a UV excitation filter block. All microscopic counts were determined in duplicate, with a minimum of 300 cells counted per assay.

Special pre-treatment procedure for the in situ hybridisation of *lactobacillus* spp.

Most bacteria exhibit high levels of fluorescence when hybridised with fluorescent probes (Langendijk et al., in press). However, members of the genus Lactobacillus are difficult to hybridize. Pure cultures of this genus exhibit a very low level of fluorescence and, in general, less than 50% of the cells exhibits fluorescence above background values (Langendijk et al., in press). Such results have also been reported for Gram-positive cocci such as *lactococci, streptococci* and *enterococci* (Beimfohr et al, 1993, Salama et al., 1991). That the poor permeability of these cells is not solely due to their Gram-positive nature is demonstrated by the fact that both clostridia and bifiodobacteria exhibit high fluorescence signals with 16 S probes when using standard hybridization conditions (Langendijk et al., in press).

We have developed a protocol for whole cell in situ hybridization of *lactobacilli*. In this protocol, standard whole-cell fluorescence in situ hybridization (FISH) protocols are preceded by a lysozyme/lipase treatment as follows. Determination of specificity of the Lab probe:

Cell of 1 ml of mid-log cultures of 10 Lactobacillus strains and a total of 26 reference stains (see tables 2 and 3), were washed in PBS and resuspended in 1 ml of pre-lysis buffer. The PBS consisted of 8 g.l$^{-1}$ NaCl, 0.2 g.l$^{-1}$ KCl, 1.44 g.l$^{-1}$ Na$_2$HPO$_4$ and 0.24 g.l$^{-1}$ KH$_2$PO$_4$. The pre-lysis buffer consisted of 50 mM Tris (pH 7.5); 10 mM EDTA; 0.585 M sucrose; 5 mM CaCl$_2$; 0.3 mg.ml$^{-1}$ sodium taurocholate; 5 mg.ml$^{-1}$ lysozyme and 0.031 mg.ml$^{-1}$ pancreatic lipase. Cells were incubated for 1 h at 37° C., washed in PBS and fixed in ethanol-PBS (1:1) for 1 h. Ten microliter of this suspension was dried on a glass slide and heat-fixed. The cells smears were dehydrated in a graded ethanol series (70% and 96%, 3 min each). Ten μl of hybridisation buffer and 1 μl of FITC-labelled probe (50. μl$^{-1}$) was added to the smears. The hybridization buffer consisted of 0.9 M NaCl, 20 mM Tris-HCl (pH 7.5) and 0.1% (w/v) sodium dodecyl sulphate. The smears were covered with a coverslip and the slides were incubated at 50° C. for 16 h in a buffer-saturated hybridisation chamber. Subsequently, the slides were washed for 30 min in 50 ml hybridization buffer at 50° C., air-dried and mounted in Vectashield (Vector Laboratories, Inc. Burlingame, Calif.). This treatment resulted in hybridization percentages of over 90%.

TABLE 1

Bacterial species included in the determination of the specificity of the various probes.
All 15 probes (except for the Lab probe [see below]) are being tested against all of the bacteria indicated. Positive hybridization results (obtained of anticipated) are marked by XXX.

| SPECIES | REC | CYL | PEP | RUM | LIT | ANA | FUS | HIS | LAB | STR | FRA | DIS | ATO | LEP | BIF |
|---|---|---|---|---|---|---|---|---|---|---|---|---|---|---|---|
| *Atopobium minutum* | | | | | | | | | | | | | XXX | | |
| *Bacteroides distasonis* | | | | | | | | | | | | XXX | | | |
| *Bacteroides eggerthii* | | | | | | | | | | | XXX | | | | |
| *Bacteroides fragilis* | | | | | | | | | | | XXX | | | | |
| *Bacteroides thetaiotamicron* | | | | | | | | | | | XXX | | | | |

TABLE 1-continued

Bacterial species included in the determination of the specificity of the various probes.
All 15 probes (except for the Lab probe [see below]) are being tested against all of the
bacteria indicated. Positive hybridization results (obtained of anticipated) are marked by XXX.

| SPECIES | REC | CYL | PEP | RUM | LIT | ANA | FUS | HIS | LAB | STR | FRA | DIS | ATO | LEP | BIF |
|---|---|---|---|---|---|---|---|---|---|---|---|---|---|---|---|
| *Bacteroides uniformis* | | | | | | | | | XXX | | | | | | |
| *Bacteroides vulgatus* | | | | | | | | | XXX | | | | | | |
| *Bifidobacterium adolescencis* | | | | | | | | | | | | | | | XXX |
| *Bifidobacterium angulatum* | | | | | | | | | | | | | | | XXX |
| *Bifidobacterium animalis* | | | | | | | | | | | | | | | |
| *Bifidobacterium asteroides* | | | | | | | | | | | | | | | XXX |
| *Bifidobacterium breve* | | | | | | | | | | | | | | | XXX |
| *Bifidobacterium bifidum* | | | | | | | | | | | | | | | XXX |
| *Bifidobacterium boum* | | | | | | | | | | | | | | | XXX |
| *Bifidobacterium cornutum* | | | | | | | | | | | | | | | XXX |
| *Bifidobacterium densium* | | | | | | | | | | | | | | | XXX |
| *Bifidobacterium globosum* | | | | | | | | | | | | | | | XXX |
| *Bifidobacterium infantis* | | | | | | | | | | | | | | | XXX |
| *Bifidobacterium longum* | | | | | | | | | | | | | | | XXX |
| *Bifidobacterium magnum* | | | | | | | | | | | | | | | XXX |
| *Bifidobacterium pseudolongum* | | | | | | | | | | | | | | | XXX |
| *Bifidobacterium subtile* | | | | | | | | | | | | | | | XXX |
| *Bifidobacterium suis* | | | | | | | | | | | | | | | XXX |
| *Clostridium aminovalericum* | XXX | | | | | | | | | | | | | | |
| *Clostridium barast* | | | | | | | | XXX | | | | | | | |
| *Clostridium beijerinckii* | | | | | | | | XXX | | | | | | | |
| *Clostridium bifermensans* MLS | | | | | XXX | | | | | | | | | | |
| *Clostridium butyricum* | | | | | | | | XXX | | | | | | | |
| *Clostridium carnis* | | | | | | | | XXX | | | | | | | |
| *Clostridium clostridiiforme* | XXX | | | | | | | | | | | | | | |
| *Clostridium cochlearium* | | XXX | | | | | | | | | | | | | |
| *Clostridium indolis* | | | | | | | | | | | | | | | |
| *Clostridium innocuum* | | XXX | | | | | | | | | | | | | |
| *Clostridium perfringens* | | | | | | | | XXX | | | | | | | |
| *Clostridium paraputrificum* | | | | | | | | XXX | | | | | | | |
| *Clostridium putrificum* | | | | | | | | XXX | | | | | | | |
| *Clostridium scatalogenes* | | | | | | | | XXX | | | | | | | |
| *Clostridium splanchnicus* | | | | | | | | | | | | | | | |
| *Clostridium sporosphaeroides* | | | | | | | | | | | | | | XXX | |
| *Enterococcus faecalis* | | | | | | | | | XXX | | | | | | |
| *Enterococcus faecium* | | | | | | | | | | | | | | | |
| *Eubacterium aerofaciens* | | | | | | | | | | | | | | | |
| *Eubacterium budayi* | | | | | | | | XXX | | | | | | | |
| *Eubacterium contortum* | XXX | | | | | | | | | | | | | | |
| *Eubacterium cilindroides* | | XXX | | | | | | | | | | | | | |
| *Eubacterium formicigenerans* | XXX | | | | | | | | | | | | | | |
| *Eubacterium lensum* | | | | | | | | | | | | | XXX | | |
| *Eubacterium moniliforme* | | | | | | | | XXX | | | | | | | |
| *Eubacterium nitrinogenes* | | | | | | | | XXX | | | | | | | |
| *Eubacterium rectale* | XXX | | | | | | | | | | | | | | |
| *Eubacterium ruminantium* | | | | | | | | | | | | | | | |
| *Eubacterium siraeum* | | | | | | | | | | | | | | XXX | |
| *Eubacterium tenue* | | | | | XXX | | | | | | | | | | |
| *Eubacterium tortmosum* | | XXX | | | | | | | | | | | | | |
| *Eubacterium ventriosum* | XXX | | | | | | | | | | | | | | |
| *Fusobacterium mortiferum* | | | | | | | XXX | | | | | | | | |
| *Fusobacterium necrophorum* | | | | | | | XXX | | | | | | | | |
| *Fusobacterium vanium* | | | | | | | XXX | | | | | | | | |
| *Lactobacillus acidophilus* | | | | | | | | | XXX | | | | | | |
| *Lactobacillus bravis* NZT01 | | | | | | | | | XXX | | | | | | |
| *Lactobacillus casei* subsp. *casei* | | | | | | | | | XXX | | | | | | |
| *Lactobacillus delbrueckii* supsp. *lactis* | | | | | | | | | XXX | | | | | | |
| *Lactobacillus fermentum* | | | | | | | | | XXX | | | | | | |
| *Lactobacillus helveticus* HP | | | | | | | | | | | | | | | |
| *Lactobacillus plantarum* | | | | | | | | | XXX | | | | | | |
| *Lactobacillus salivarius* subsp. *salicinius* | | | | | | | | | XXX | | | | | | |
| *Lactococcus lactis* susbp. *lactis* P15 | | | | | | | | | | XXX | | | | | |
| *Leuconostoc lactis* C17 | | | | | | | | | | XXX | | | | | |
| *Peptococcus asaccharotysicus* | | | | | | | | | | | | | | | |
| *Peptostreptococcus anaerobius* | | | | | | XXX | | | | | | | | | |
| *Peptostreptococcus micros* | | | XXX | | | | | | | | | | | | |
| *Peptostreptococcus tetradius* | | | XXX | | | | | | | | | | | | |
| *Propionibacterium acnes* | | | | | | | | | | | | | | | |
| *Ruminobacter amylophilus* | | | | | | | | | | | | | | | |
| *Ruminococcus hansenil* | XXX | | | XXX | | | | | | | | | | | |
| *Ruminococcus productus* | | | | XXX | | | | | | | | | | | |
| *Streptococcus bovis* | | | | | | | | | | XXX | | | | | |

TABLE 1-continued

Bacterial species included in the determination of the specificity of the various probes.
All 15 probes (except for the Lab probe [see below]) are being tested against all of the
bacteria indicated. Positive hybridization results (obtained of anticipated) are marked by XXX.

| SPECIES | REC | CYL | PEP | RUM | LIT | ANA | FUS | HIS | LAB | STR | FRA | DIS | ATO | LEP | BIF |
|---|---|---|---|---|---|---|---|---|---|---|---|---|---|---|---|
| *Streptococcus bovis* | | | | | | | | | | XXX | | | | | |
| *Streptococcus equinus* | | | | | | | | | | XXX | | | | | |
| *Streptococcus intermedius* | | | | | | | | | | XXX | | | | | |
| *Streptococcus mutans* (DSM) | | | | | | | | | | XXX | | | | | |
| *Streptococcus mutans* (SLL) | | | | | | | | | | XXX | | | | | |
| *Streptococcus salivarius* subsp. ?? | | | | | | | | | | XXX | | | | | |
| *Streptococcus sanguis* | | | | | | | | | | XXX | | | | | |

TABLE 2

Reference strains used for specificity tests of the Lab probe

| Name: | Origin |
|---|---|
| *Bacteroides distasonis* | MMB 3335 |
| *Bacteroides fragilis* | MMB 3407 |
| *Bacteroides thetaiotaomicron* | RPHL 2 |
| *Bifidobacterium adalescentis* | NIZO B659 |
| *Bifidobacterium infantis* | ATCC 15697 |
| *Bifidobacterium longum* | MMB 3277 |
| *Clostridium beijerinckii* | MMB 3318 |
| *Clostridium bifermentans* | NIZO B529 |
| *Clostridium carnis* | DSM 1293 |
| *Enterococcus faecalis* | MMB 2405 |
| *Enterococcus faecium* | SLL 4 |
| *Eubacterium aerofaciens* | DSM 3979 |
| *Eubacterium cylindroides* | MMB 3291 |
| *Eubacterium lentum* | ATCC 25559 |
| *Eubacterium rectale* | ATCC 33656 |
| *Fusobacterium mortiferum* | MMB 3040 |
| *Fusobacterium necrophorum* | MMB HB130 |
| *Lactococcus lactis* subsp. *lactis* P15 | NIZO B1 |
| *Leuconostoc lactis* C17 | NIZO B630 |
| *Peptococcus asaccharolyticus* | MMB 3351 |
| *Peptostreptococcus anaerobius* | MMB 2828 |
| *Peptostreptococcus micros* | DSM 20468 |
| *Ruminococcus productus* | DSM 2950 |
| *Streptococcus bovis* | SLG 1 |
| *Streptococcus equinus* | SLL 5 |
| *Streptococcus intermedius* | DSM 20573 |

TABLE 3

Lactobacillus Strains used for specificity tests of the Lab probe

| Name | Origin |
|---|---|
| *Lactobacillus acidophilus* | DSM 20077 |
| *Lactobacillus brevis* NZT01 | NIZO B306 |
| *Lactobacillus casei* subsp. *casei* | MMB 3225 |
| *Lactobacillus delbrueckii* subsp. *lactis* | NIZO B193 (ATCC 800) |
| *Lactobacillus fermentum* | MMB 3289 |
| *Lactobacillus helveticus* HP | NIZO B210 |
| *Lactobacillus leichmannii* | MMB 3269 |
| *Lactobacillus plantarum* Qg | NIZO B253 |
| *Lactobacillus ruminis* | DSM 20403 |
| *Lactobacillus salivarius* subsp. *salicinius* | DSM 20554 |

Whole cell in situ hybridization and enumeration of *lactobacilli* in faecal samples For enumeration of *lactobacilli* in faecal samples, the same protocol was followed as described under "Whole cell in situ hybridization and enumerating of phylogenetic clusters in faecal samples", except that prior to dilution of the paraformaldehyde-fixed and washed cell suspensions in 50% ethanol, cells were resuspended in pre-lysis buffer and incubated at 37° C. for 1 hr. Cells were washed twice ((8,000×g; 5 min) in 1 ml of filtered PBS and resuspended in 1 ml of a mixture of PBS and ethanol (1:1) and hybridized in solution as described above.

RESULTS

Upon phylogenetic analysis, the predominant bacterial species of the human intestinal flora were distributed over 15 separate clusters. Some of these clusters constituted monophyletic genera, such as Bifidobacterium and Fusobacterium. Other were composed of a mixture of Eubacterium, Clostridium, and Peptostreptococcus spp., as in case of the *Clostridium coccoides* group (Larsen et al., 1993). Unique sequences for each of these separate clusters were identified, and the percentage of the total population that the probe would hybridize to was evaluated. In the case that a certain species was expected to consist a major part of the population, such as *Peptostreptococcus anaerobius*, or when a species could not be included in a cluster-probe such as *Bacterioides distasonis*, species-specific probes were developed.

The following probes were developed:

1. The *Clostridium hystolyticum* subgroup probe His5 (TTATGCGGTATTAATCT (TC) CCTT) Td=56.5–58.4° C., has a full match with *Clostridium putrificum, C. butyricum, C. barati, C. carnis, C. botulinum, C. novyi, C. sporogenes, C. putrificum, C. tyrobytyricum, C. scatologenes, C. scatologenes, C. proteolyticum, C. limosum, C. sardiniensis, C. perfringens, C. beijerinckii, C. acebutylicum, C. puniceum, C. cellulovorans, C. paraputrificum, C. thermobuityricum, C. thermopalmarium, C. subterminale, C. argentinense, C. estertheticum, C. pasteurianum, C. histolyticum, Eubacterium budayi, E. delafieldii, E. moniliforme, E. multiforme, E. nitritogenes, E. tarantellus* and *Flexibacter canadensis*.

2. The *Clostridium lituseburense* subgroup probe Lit135 (GTTATCCGTGTGTACAGGG), Td=59.2° C., has a full match with *Eubacterium tenue, Clostridium difficile, C. bifermentans, C. sordellii, C. ghoni, C. lituseburense* and *C. mangenotti*.

3. The Peptostreptococcus probe Pep197 (TCTTACACCGATAAACTTTG), Td=55.4° C., has a full match with *Peptostreptococcus micros, P. tetradius, P. vaginalis* and *Epilopiscium morphotye* A1.

4. The Peptostreptococcus probe Ana134 (ATGTTATCCATGTGTATAGGGC), Td=60.2° C., has a full match with *Peptostreptococcus anaerobius* and *Peptostreptococcus sp. C*.

5. The Fusobacterium genus probe Fus390 (CACACAGAATTGCTGGATC), Td=60.2° C., has a a full match with *Fusobacterium simiae, F. nucleatum, F. alocis, F. russii, F. gonidoformans, F. necrophorum, F. varium, F. mortiferum, F. perfoetens, Propionigenium modestum, Leptotrichia buccalis* and *Sebalcella termitidis*. The probe may also hybridize to *F. ulcerans, F. periodonticum* and *F. necrogenes* since these bacteria have one unknown base in the target region.

6. The Lactobacillus subgroup probe Lab158 (GGTATTAGCA (TC) CTGTTTCCA), Td=56.1–58.2° C., has a a full match with *Lactobacillus acidophilus, L. acidophilus* subsp. *johnsonii, L. delbrueckii* subsp. *lactis, L. delbrueckii* subsp. *delbrueckii, L. brevis, L. salivarius* subsp. *salicinius, L. amylovorus, L. acetotolerans, L. oris, L. hilgardii, L. kefir, L. mali, L. animalis, L. murinus, L. ruminis, L. agilis, L. sharpeae, L. gasseri, L. amylophilus, L. reuteri, L. fermentum, L. sake, L. sanfrancisco, L. fructivorans, L. plantarum L. bifermentans, L. coryniformis, L. casei* subsp. *casei, L. casei* subsp. *rhamosus, Leuconostoc lactis, Lc. mesenteroides* subsp. *mesenteroides, Lc. mesenteroides* subsp. *cremoris, Lc. oenos, Enterococcus faecalis, E. columbae, Periococcus pentosaceus, P. acidilactici, Streptococcus cecorum, Vagococcus fluvialis, V. salmoninarium, Weissella confusa* and *W. kandleri*.

7. The Streptococcus/Lactococcus probe Str493 (GTTAGCCGTCCCTTTCTGG), Td=61.3° C., has a full match with *Streptococcus sanguis, S. salivarius, S. bovis, S. pneumoniae, S. parasanguis, S. acidominimus, S. dysgalactiae, S. anginosus, S. vestibulariis, S. equinus, S. alactolytiens, S. downei, S. sobrinus, S. rattus, S. cricetus, S. hyointestinalis, S. agalactiae, S. suis, S. porcinus, S. canis, S. pyogenes, Lactococcus lactis* subsp. *lactis, L. lactis* subsp. *cremoris, L. piscium, L. raffinolactis, L. plantarium, L. garvieae*. The probe may also be used to detect *Streptococcus oralis, S. intermedius, S. macacae, S. mutans, S. anginosus, S. criae* and *S. equi* since these bacteria contain one or two unknown bases in the target region.

8. The *Bacteroides vulgatus* assemblage probe Fra602 (GAGCCGCAAACTTTCACAA), Td=57° C., has a full match with *Bacteroides eggertii, B. thetaiotaomicron, B. ovatus, B. fragilis, B. uniformis* and *B. vulgatus*.

9. The *Bacteroides distasonis* species Dis657 (CCGCCTGCCTCAAACATA), Td=58.0° C., has a full match with *Bacteroides distasonis*.

10. The Mycoplasma's walled relatives group II probe Cyl387 (CGCGGCATTGCTCGTTCA), Td=60.2° C., has a full match with *Eubacterium cylindroides, E. tortuosum, E. dolichum, E. biforme, Clostridium innocuum* and *Streptococcus plemorphus*.

11. The Atopobium subgroup probe Ato292 (GGTCGGTCTCTCAACCC), Td=59.0° C., has a full match with *Atopobium minucum A. parvulum, A. rimae, Eubacterium lentum* and possibly als. *E. fosser* (one unknown base in target region).

12. The *Clostridium coccoides* group probe Rec484 (GCTTCTTAGTCA (AG)GTACCG), Td=59.2° C., has a full match with *Eubacterium contortum, E. formicigenerans, E. rectale, E. ventriosum, E. cellulosolvens, E. eligens, E. fissicatena, E. hadrum, E. halii, E. saburreum, E. uniforme, E. ventriosum, E. xylanophilum, Clostridium aminovalericum, C. clostridiiforme, C. nexile, C. oroticum, C. lentocellum, C. symbiosum, C. aminophilumn, C. xylanolyticum, C. sphenoides, C. celarecrescens, Ruminococcus hansenii,* Epulopiscium sp. str. morphotypes A2 and *B. Acetitomaculum ruminis, Lachnospira pectinoschiza, L. multiparus, Roseburia cecicola* and possibly also with *Clostridium coccoides* (unknown base).

13. The Ruminiococcus probe Rum186 (TTCACACCAGACCATGCG), Td=58.0° C. has a full match with Ruminococcus products and *Ruminococcus hansenii*.

14. The *Clostridium leptum* subgroup probe Lep has a full match with *Eubacterium siraeum, E. plautii, E. desmolans, Clostridium sporosphaeroides, C. leptum* and *C. cellulosi*.

15. The Bifidobacterium genus probe Bif164 (CATCCGGCATTACCACCC), Td=60.2° C., has a full match with *Bifidobacterium longum, B. pseudolongum, B. suis, B. infantis, B. indicum, B. breve, B. adolescents, B. catenulatum, B. minimum* and possibly also to *B. bifidum, B. dentium, B. coryneforme, B. asteroides, B. globosum, B. magnum* and *Gardnerella vaginalis* since these bacteria have one or more unknown bases in the target region.

These 15 clusters were chosen as indicated in FIG. 1. Melting temperatures (Td) are theoretical values. Hybridization will usually occur at temperatures about 1–5° C. below these values. Sequences are 5'-3'.

REFERENCES

1. Amman, R. I., W. Ludwig and K. H. Schleifer. 1995. Phylogenetic identification of individual microbial cells without cultivation. Microbiol. Rev. 59:143–169.

2. Beimfohr, C., A. Krause, R. Amann, W. Ludwig and K. H. Schleifer. 1993. in situ identification of *lactococci, enterococci* and *sterptococci*. Syst. Appl. Microbiol. 16:140–456.

3. Drasar, B. S. and P. A. Barrow. 1985. Intestinal Microbiology. Aspects of Microbiology 10. American Society for Microbiology, Washington, U.S.A.

4. Finegold, S. M., H. R. Attebery and V. L. Sutter. 1974. Effect of diet on human fecal flora; comparison of Japanese and American diets. Am. J. Clin. Nutr. 27:1456–1469.

5. Holdeman, L. V., E. P. Cato and W. E. C. Moore, 1997. Anaerobe Laboratory Manual, 4th ed. Virginia Polytechnic Institute and State University, Blacksburg, Va.

6. Jansen, G. J., M. H. F. Wilkinson, B. Deddens and D. van der Waaij. 1993. Characterization of human faecal flora by means of an improved fluoromorphometrical method. Epidemiol. Infect. 111:265–272.

7. Kurat, S., K. Tamura and M. Nei. 1993. MEGA: Molecular Evolutionary Genetics Analysis, version 1.01. The Pennsylvania State University, University Park, Pa.

8. Larsen, N., G. J. Olsen, B. L. Maidak, M. J. McCaughey, R. Overbeek, T. J. Macke, T. L. Marsh and C. R. Woese. 1933. The ribosomal database project. Nucleic Acids Res. 21:3021–3023.

9. Meijer, B. C., G. J. Kootstra, D. G. Geertsma and M. H. F. Wilkinson. 1991. Effects of certriaxone on faecal flora; analysis by micromorphometry, Epidemiol. Infect. 106:513–521.

10. Porter, K. G. and Y. S. Feig. 1980. The use of DAPI for identifying and counting aquatic microflora. Limnol. Oceanogr. 25:943–948.

11. Salama, M., W. Sandine and S. Giovannoni. 1991. Development and application of oligonucleotide probes for identification of *Lactococcus lactis* subsp. *cremoris*. Appl. Environ. Microbiol. 57:1313–1318.

12. Sutter, V. L., D. M. Citron, M. A. C. Edelstein and S. M. Finegold. 1985. Wadsworth anaerobic Bacteriology Manual, 4th ed. Star Publ. Corp., Belmont, Calif.

13. Van der Waaij, D., J. M. Berghuis-de Vries and J. E. C. Lekkerkerk-van der Wees. 1971. Colonization resistance of the digestive tract in conventional and antibiotic-treated mice. J. Hyg. 67:405–411.

14. Van der Waaij, D. 1989. The ecology of the human intestine and its consequences for overgrowth by pathogens such as *Clostridium difficile*. Ann. Rev. Microbiol. 43:67–87.

15. Wilkinson, M. H. F. 1994. Shading correction and calibration in bacterial fluorescence measurement by image processing system. Comput. Methods Programs Biomed. 44:61–67.

16. Wilkinson, M. H. F., G. J. Jansen and D. van der Waaij. 1993. Very low level fluorescence detection and imaging using a long exposure charge coupled device system, p. 221–230. In: P. H. Bach, C. H. Reynolds, J. M. cClark, J. Mottley and P. L. Poole (ed.), Biotechnology application of micro-injection, microscopic imaging and fluorescence. Pergamon Press, New York.

17. Wilkinson, M. H. F., G. J. Jansen and D. van der Waaij. 1994. Computer processing of microscope images of bacteria; morphometry and fluorimetry. Trends Microbiol. 2:485–489.

What is claimed is:

1. A method for determining the relative abundance of individual species or lower phylogenetic subgroups of microorganisms in a mixed population of several microorganisms which comprises the steps of
   1) preparing a set of labelled in situ hybridization cluster oligonucleotide probes;
   2) effecting hybridization of said probes with a sample of the mixed population by contacting a cell suspension derived from said sample with a hybridization buffer comprising said probes, thereby hybridizing said cells, and
   3) effecting quantitative analysis of the number of labelled microorganisms by enumeration of various phylogenetic groups of said microorganisms.

2. A method according to claim 1, wherein the probes are labelled with a fluorescent material.

3. A method according to claim 1, wherein the probes are based on 16S rRNA of target microorganisms.

4. A method according to claim 1 wherein the quantitative analysis is performed by microscopic image analysis.

5. A method according to claim 1 wherein the probes are specific for a phylogenetic cluster of microorganisms.

6. A method according to claim 5 wherein the phylogenetic cluster is a genus or a species.

7. A method according to claim 1 wherein the microorganisms are bacteria.

8. A method according to claim 1 wherein the mixed population is the indigenous gut flora, particular of a mammal, especially a human.

9. A method for analyzing dynamics in relative abundance of individual microorganisms in a mixed population whereby a method according to claim 1 is carried out at least twice on samples taken at a different time from one population.

10. A method according to claim 1 wherein the sample is pretreated and/or purified.

11. A method according to claim 1 wherein at least two different probes are provided with a different label.

12. A set of probes which are cluster specific and which are provided with at least one label for use in a method according to claim 1.

13. A set of probes according to claim 12 being derived from bacterial 16S rRNA.

14. A set of probes according to claim 12, whereby the label is a fluorescent substance.

15. A set of probes according to claim 12 comprising at least two different probes provided with different labels.

16. A kit of parts for determining the relative abundance of individual species of microorganisms in a mixed population of several microorganisms comprising a set of probes according to claim 12 together with suitable materials for pretreating the sample and/or suitable materials for carrying out hybridization and/or suitable materials for analysis of the result of the hybridization.

* * * * *